(12) United States Patent
Parker

(10) Patent No.: US 6,998,452 B1
(45) Date of Patent: Feb. 14, 2006

(54) CONTROLLED FREE RADICAL AGENT FOR NANOCOMPOSITE SYNTHESIS

(75) Inventor: Dane Kenton Parker, Massillon, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 11/036,407

(22) Filed: Jan. 14, 2005

(51) Int. Cl.
C08F 2/38 (2006.01)
C07F 7/04 (2006.01)

(52) U.S. Cl. ............. 526/194; 526/335; 526/340; 524/445; 524/571; 524/575; 501/129; 501/133; 501/141; 501/148; 556/429

(58) Field of Classification Search .......... 556/429; 501/129, 133, 141, 148; 526/194, 335, 340; 524/445, 571, 575; 152/209.1
See application file for complete search history.

(56) References Cited

U.S. PATENT DOCUMENTS

| | | | |
|---|---|---|---|
| 5,405,985 A | 4/1995 | Parker et al. | 556/427 |
| 5,468,893 A | 11/1995 | Parker et al. | 556/427 |
| 5,583,245 A | 12/1996 | Parker et al. | 556/427 |
| 5,663,396 A | 9/1997 | Musleve et al. | 556/427 |
| 6,172,251 B1 | 1/2001 | Parker | 556/427 |
| 6,384,255 B1 | 5/2002 | Backer et al. | 556/427 |
| 6,384,256 B1 | 5/2002 | Backer et al. | 556/427 |
| 6,448,426 B1 | 9/2002 | Backer et al. | 556/427 |
| 6,534,668 B1 | 3/2003 | Backer et al. | 556/427 |
| 6,680,398 B1 | 1/2004 | Boswell et al. | 556/429 |
| 6,759,464 B1 | 7/2004 | Ajbani et al. | 524/445 |
| 6,861,462 B1 * | 3/2005 | Parker et al. | 524/445 |
| 2003/0055139 A1 * | 3/2003 | Cruse | 524/262 |
| 2003/0232938 A1 * | 12/2003 | Charmot et al. | 526/194 |
| 2004/0054059 A1 | 3/2004 | Parker et al. | 524/445 |
| 2004/0127634 A1 | 7/2004 | Parker et al. | 524/571 |

OTHER PUBLICATIONS

Prokopov and Gritskova (*Russ. Chem. Rev* 2001, 70, 791).

* cited by examiner

Primary Examiner—Fred Teskin
(74) Attorney, Agent, or Firm—Alvin T. Rockhill

(57) ABSTRACT

This invention relates to a process for producing a free radical control agent of the structural formula:

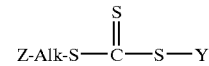

wherein Z is selected from the group consisting of

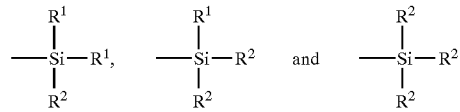

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition; said process comprising the steps of (1) reacting a mercaptosilane of the structural formula: Z-Alk-SH with carbon disulfide in the presence of a phase transfer catalyst and an alkali metal hydroxide to produce a trithiocarbonate salt; and (2) reacting the trithiocarbonate salt with a halogen containing compound of the structural formula X-Y to produce the free radical control agent, wherein X represents a halogen atom. Such free radical control agents are capable of covalently bonding to silica/silicate surfaces and are of particular benefit in producing rubbery compounds that will be loaded with silica fillers, such as tire tread rubbers.

18 Claims, No Drawings

CONTROLLED FREE RADICAL AGENT FOR NANOCOMPOSITE SYNTHESIS

BACKGROUND OF THE INVENTION

In recent years, there has been intense interest concerning the grafting of polymers to inorganic surfaces. Such grafting can be accomplished by anionic, cationic or free radical processes. Among these processes, living (controlled) free radical polymerization (CFRP) has been shown to have an overwhelming advantage over other surface grafting methods in that it allows grafting of homo- and copolymers of controlled structure and molecular weight with a very high grafting density. Examples of all three major CFRP systems (ATRP, NMP and RAFT) have been successfully demonstrated using a "grafting from" technique for the preparation of organic-inorganic (O/I) nanocomposites.

The process by which the vast majority of O/I nanocomposites have been generated thus far utilizing CFRP methods and silica/silicate precursors usually involves two steps; first, a functionalization of the silica/silicate surface with a CFR agent by an ionic or covalent bond (remote from the attached CFR functional group). This reaction is most often conducted in bulk or in a solvent. Second, the CFR-functionalized silica/silicate is then suspended in a monomer (eg. styrene, acrylate etc.) in the presence of a free radical initiator. As the polymerization proceeds from the particle surfaces, the organic dispersability of the O/I composite improves dramatically. Unfortunately, such solution CFR polymerizations are typically very slow and give incomplete monomer conversion. This necessitates long reaction times and difficult monomer recovery.

Another widely used technique for the preparation of O/I nanocomposites utilizes the more rapid and environmentally friendly technique of emulsion polymerization and/or latex blending. Numerous variations on this method have been demonstrated. Typical of this method is the more-or-less conventional free radical polymerization of a monomer(s) in the presence of a highly dispersed surface-modified nano-size silica/silicate inorganic component. Alternatively, various techniques to combine preformed rubber latex (an aqueous dispersion of rubber nanoparticles) with aqueous dispersions of nanosized silica/silicates followed by coagulation will yield the nanocomposite. U.S. Pat. No. 6,759,464 and U.S. Patent Application 2004/0054059 describe some examples of technology in this area. While significant benefits can be obtained using these systems, control over the molecular weight, composition and polydispersity of the organic (polymer) component of the composite is lacking.

Therefore, the need still exists to develop practical methods whereby the best features of CFRP technology (e.g. control over the molecular weight, composition and polydispersity) can be combined with the simplicity of an emulsion process to yield useful nanocomposites materials.

U.S. Pat. No. 5,405,985, U.S. Pat. No. 5,468,893, U.S. Pat. No. 5,583,245, U.S. Pat. No. 5,663,396, and U.S. Pat. No. 6,172,251, as well as subsequent improvement patents (U.S. Pat. No. 6,680,398, U.S. Pat. No. 6,534,668; U.S. Pat. No. 6,448,426; U.S. Pat. No. 6,384,256, and U.S. Pat. No. 6,384,255) disclose the utilization of aqueous phase transfer technology for the preparation of sulfur-containing alkoxysilanes.

SUMMARY OF THE INVENTION

As has been explained, various CFRP systems have been used in the preparation of O/I nanocomposites. Perhaps the most versatile and robust of these systems is RAFT (Reversible Addition-Fragmentation Transfer). The key to its activity in the CFRP mechanism is a process called "degenerative transfer" whereby propagating polymeric radicals react efficiently with either a dithioester or trithiocarbonate group in the CFR agent to form an intermediate stabilized radical species that rapidly fragments to generate a new radical species capable of reinitiating polymerization. As this process continues, the polymer incorporates the CFR functional group by repeated chain transfer reactions resulting in a polymer of controlled molecular weight and polydispersity. By proper-design of the CFR RAFT agent to include both the thioester functionality and a functional group reactive toward the surface silanol groups on silica/silicate materials or ion exchange in case of certain layered silicates, a surface bound RAFT species can be prepared.

Using the aqueous phase transfer technology employed in the preparation of sulfur-containing alkoxysilanes a procedure has been developed to prepare S-(3-triethoxysilylpropyl)-S'-benzyl trithiocarbonate (TSPBT) as a prototypical dual functional RAFT agent capable of covalent bonding to a silica/silicate surface. The driving force behind the efforts to prepare O/I nanocomposites has been the unique combination of outstanding and special properties of such composites that are difficult or impossible to obtain with non-composite materials. Some demonstrated properties of O/I nanocomposites are chemical stability, thermal stability, gas barrier properties, low density, melt processibility, toughness and reinforcement ability. Many of these properties find particular utility in highly engineered products especially belts, hoses and tires. Currently, most of this work has focused on the use of either colloidal silica particles or layered silicates (clays) as the inorganic component of the composite due to their nano-size structures and low cost, however, carbon nanotubes, metal and metal oxides nanoparticles may also be used. The use of CFR methodologies further expands the utility of O/I nanocomposites by allowing a wide variety of well-defined structures to be readily synthesized.

Although numerous CFRP and other techniques have been investigated for the synthesis of well dispersed O/I nanocomposites, heretofore the synthesis of this particular class of silane-functional RAFT agents or their use in the preparation of O/I nanocomposites has been unknown. Furthermore, although there now exist several aqueous-based phase transfer processes for the preparation of sulfur-containing silanes, the process of this invention offers the first preparation of alkoxysilane dithioesters and trithiocarbonates capable of participation in CFRP systems.

This invention more specifically discloses a free radical control agent of the structural formula:

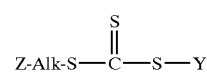

wherein Z is selected from the group consisting of

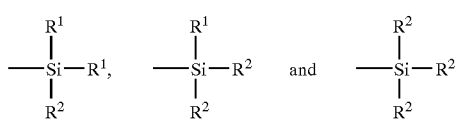

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition.

The present invention further discloses a process for producing a polymer that is capable of covalently bonding hydroxyl groups, such as a silica/silicate surface having hydroxyl functionality, which comprises polymerizing at least one monomer in the presence of a free radical control agent of the structural formula:

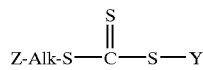

wherein Z is selected from the group consisting of

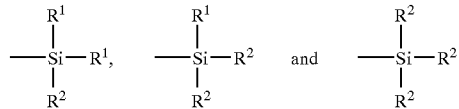

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition.

The subject invention also reveals a rubbery polymer that is capable of covalently bonding to hydroxyl groups, said rubbery polymer being comprised of repeat units that are derived from a conjugated diolefin monomer and pendant functional groups of the structural formula:

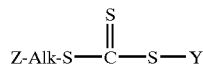

wherein Z is selected from the group consisting of

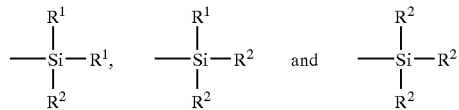

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; and wherein Alk is a divalent hydrocarbon of 1 to 18 carbon atoms.

The present invention further discloses a tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of a filler having hydroxyl surface functionality and a rubbery polymer comprised of repeat units that are derived from a conjugated diolefin monomer and pendant functional groups of the structural formula:

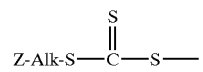

wherein Z is selected from the group consisting of

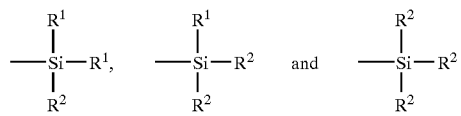

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; and wherein Alk is a divalent hydrocarbon of 1 to 18 carbon atoms.

The present invention also reveals a process for producing a free radical control agent of the structural formula:

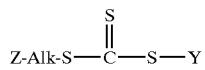

wherein Z is selected from the group consisting of

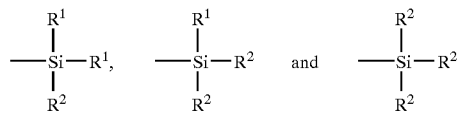

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition; said process comprising the steps of (1) reacting a mercaptosilane of the structural formula: Z-Alk-SH with carbon disulfide in the presence of a phase transfer catalyst and an alkali metal hydroxide to produce a trithiocarbonate salt; and (2) reacting the trithiocarbonate salt with a halogen containing compound of the structural formula X-Y to produce the free radical control agent.

The present invention further reveals a modified silica/silicate filler composition which is comprised of (1) a filler selected from the group consisting of silicate clays and silica; and (2) a compound of the structural formula:

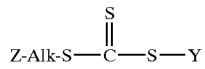

wherein Z is selected from the group consisting of

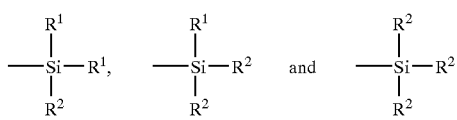

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon; wherein Alk is a divalent hydrocarbon of 1 to 18 carbon atoms; and wherein Y represents a functional group that is capable of activating a vinylic carbon toward free radical addition.

DETAILED DESCRIPTION OF THE INVENTION

By utilizing the process of this invention, dual functional RAFT agents that are capable of covalently bonding to a silica/silicate surface can be synthesized. This procedure is a multiple step process which can be depicted as follows for the preparation of S-(3-triethoxysilylpropyl)-S'-benzyl trithiocarbonate (TSPBT):

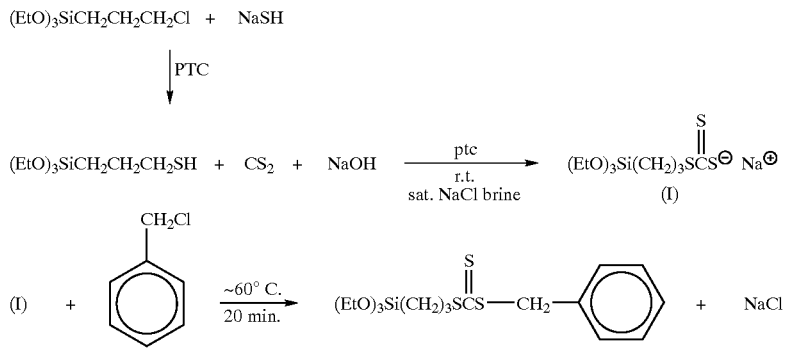

In the first step of the process a halogenated silane of the formula Z-Alk-X is reacted with a compound of the formula MeSH, wherein Z represents a member selected from the group consisting of

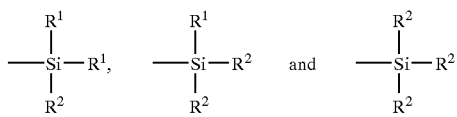

wherein $R^1$ is an alkyl group of 1 to 4 carbon atoms, cyclohexyl or phenyl; wherein $R^2$ is an alkoxy group of 1 to 8 carbon atoms or a cycloalkoxy group of 5 to 8 carbon; wherein Alk is a divalent hydrocarbon of 1 to 18 carbon atoms; wherein X represents a halogen atom, and wherein Me represents ammonium or an alkali metal.

Some representative examples of halogenated silanes of formula Z-Alk-X include the halogenated (chloro and bromo) substituted forms of ethyl triethoxy silane, propyl triethoxy silane, butyl triethoxy silane, pentyl triethoxy silane, hexyl triethoxy silane, heptyl triethoxy silane, octyl triethoxy silane, nonyl triethoxy silane, decyl triethoxy silane, undecyl triethoxy silane, dodecyl triethoxy silane, tridecyl triethoxy silane, tetradecyl triethoxy silane, pentadecyl triethoxy silane and the like.

The reaction between the halogenated silane of the formula Z-Alk-X and the sulfur containing compound, MeSH, is conducted in the presence of a phase transfer catalyst. Representative phase transfer catalysts may have a quaternary onium cation of the following structural formulae (I), (II) or (III):

(I)

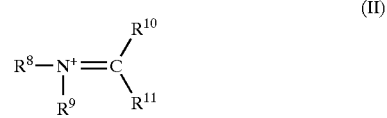

(II)

-continued

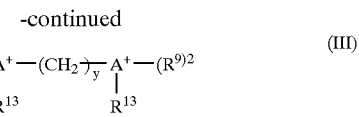

(III)

wherein A represents nitrogen, phosphorus or arsenic; $R^4$, $R^5$, $R^6$ and $R^7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms; $R^8$, $R^9$, $R^{10}$, and $R^{11}$, which also may be the same or different, are each a linear or branched chain alkyl radical containing from 1 to 4 carbon atoms; with the proviso that the $R^{10}$ and $R^{11}$ radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms which may be the same or different from $R^{12}$ or $R^{13}$ may be a linear or branched chain alkenyl radical containing from 2 to 12 carbon atoms, preferably from 4 to 8 carbon atoms, and more preferably an alkenyl radical derived by carbonylation of a conjugated diene; and y is an integer of from 1 to 10, and preferably less than or equal to 6.

Some representative examples of the quaternary onium cations of structural Formula I include the following: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium and tetraphenylarsonium.

Exemplary of the Formula II cations are the following: N-methylpyridinium, N-ethylpyridinium, N-hexadecylpyridinium and N-methylpicolinium.

Some representative examples of cations of structural Formula III include the following: 1,2-bis(trimethylammonium)ethane, 1,3-bis(trimethylammonium)propane, 1,4-bis(trimethylammonium)butane and 1,3-bis(trimethylammonium)butane.

Representative of the anions of said onium salts include the following ions: $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

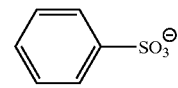

$HSO_4^-$, $NO_3^-$, $SO_4^{-2}$, $Cl^-$ and $Br^-$. Preferably, the anion is $Cl^-$ or $Br^-$. A particularly preferred onium salt that is used is tetrabutyl ammonium bromide.

A particularly preferred onium salt that can be used is methyl trialkyl ($C_8$–$C_{10}$) ammonium chloride which is commercially available under the trademark Adogen®464 from Sherex Chemical Company of Dublin, Ohio, and from Henkel Corporation, Minneapolis, Minn., under the trademark Aliquot® 336. Aliquat® 336 is a water insoluble quaternary ammonium salt made by the methylation of mixed tri octyl/decyl amine. It is composed of a large organic cation associated with a chloride ion as shown below:

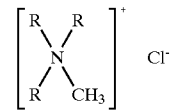

The amount of onium salt that is used in the process of the present invention may vary. Generally speaking, the amount of onium salt will range from about 0.1 to 10 mol percent relative to the halogenated silane of formula Z-Alk-X with an amount within the range of 1 to 5 mole percent being preferred.

The phase transfer catalyst may be added to the reaction at any time. From a practical standpoint, the catalyst is preferably added to the reaction mixture all at once or portionwise at a temperature which is within the range of 65° C. to 90° C. as a solid or concentrated (40–50 percent) aqueous solution.

The process of the present invention uses an aqueous system; however, one may optionally use a two phase aqueous/organic system. In fact, it is preferred to use an aqueous/organic system because the presence of the organic phase assists in the phase separation upon completion of the reaction. When the organic phase is used, preferably the silane compound is predissolved in the organic phase prior to addition to the sulfur containing compound of formula MeSH. Some representative examples of organic solvents that can be used include toluene, xylene, benzene, heptane, octane, decane, chlorobenzene and the like.

As mentioned above, the reaction between the halogenated silane of formula Z-Alk-X and the reaction mixture containing the sulfur containing compound is conducted in the presence of an aqueous phase. The volume of water that can be present may vary and may be the volume of saturated aqueous sodium chloride solution from the first reaction. The concentration of the two reactants (Z-Alk-X and MeSH) in the aqueous phase generally ranges from about 20 to 50 percent by weight. Preferably, the concentration of the sulfur containing compound in the aqueous phase ranges from about 25 to 45 percent.

For the reaction between the sulfur containing compound and the Z-Alk-X compound, additional amounts (in addition to the sodium chloride present in the brine for the first reaction) may be added. Examples of such salts include those of the formula MX and the formula $M_2SO_4$ wherein M is selected from the group consisting of lithium, sodium, potassium, rubidium and cesium; and wherein X is selected from the group consisting of fluorine, chlorine, bromine and iodine. It is normally preferred for X to represent chlorine or bromine with it being most preferred for X to represent chlorine. Representative examples of such salts include LiF, LiCl, LiBr, $Li_2SO_4$, NaF, NaCl, NaBr, $Na_2SO_4$, KF, KCl, KBr, $K_2SO_4$, RbCl, RbBr, $Rb_2SO_4$, CsCl, CsBr and $Cs_2SO_4$. Whereas the amount of salt may vary, the salt is generally present in an amount ranging from 10 percent by weight of the aqueous solution to full or complete saturation of the aqueous solution. Obviously, an excess of salt (more than full saturation) may be used; however, no additional benefit has been found. In addition, as one can appreciate, all of the various salts mentioned above have varying levels of solubility in an aqueous solution; however, the solubility of such salts is well known. In the context of saturation of the aqueous phase, it should be calculated at the desired reaction temperature since solubility of such salts in an aqueous phase is related to the temperature of the aqueous phase. Preferably, the amount of salt that is present in the aqueous phase ranges from 20 weight percent to complete or full saturation. If supplemental salt is desired, it may be added to the reaction vessel at any time so long as it is present during the reaction.

The next step in synthesizing the free radical control agent involves reacting the mercaptosilane of the structural formula: Z-Alk-SH with carbon disulfide in the presence of a phase transfer catalyst and an alkali metal hydroxide to produce a trithiocarbonate salt. This reaction will typically be conducted in the presence of a saturated sodium chloride brine and will normally be carried out at a temperature which is within the range of about 5° C. to about 50° C. This reaction will more typically be carried out at a temperature which is within the range of about 10° C. to about 30° C., such as room temperature. This reaction can be depicted as follows:

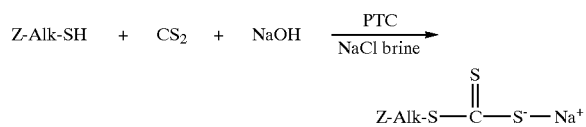

The trithiocarbonate salt is then reacted with a halogen containing compound of the formula X-Y, wherein X represents and halogen atom and wherein Y represents a functional group that is capable of activating a vinylic carbon toward free radical addition, to produce the free radical control agent. Some representative examples of Y groups include: —C(R')$_2$CN, —C(CH$_3$)$_2$Ar, —C(CH$_3$)$_2$COOR", —C(CH$_3$)$_2$CONHR", —C(CH$_3$)$_2$CH$_2$C(CH$_3$), —CH(CH$_3$)Ar, —CH$_2$Ar, —C(CH$_3$)$_3$, —CR'$_2$COOH, —C(R')(CN)(CH$_2$)$_n$COOH, and C(R')(CN)—(CH$_2$), —OH; wherein R' represents a linear or branched hydrocarbon containing from 1 to 12 carbon atoms; wherein R" represents an alkyl group containing from 1 to about 8 carbon atoms, wherein Ar represents an unsubstituted or substituted phenyl, napthyl, anthracenyl, or pyrenyl group; and wherein n represents an integer from 1 to 8. It is preferred for R" to represent an alkyl group containing from 1 to 4 carbon atoms. This reaction will typically be conducted at a temperature which is within the range of about 20° C. to about 95° C. and will preferably be conducted at a temperature which is within the range of 40° C. to 80° C. This reaction can be depicted as follows:

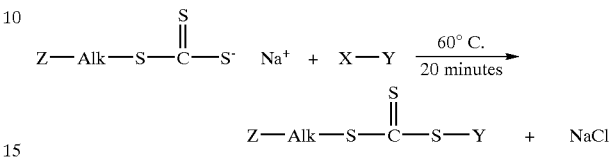

The free radical control agent can then be used in conducting controlled polymerizations to produce polymers that may be capable of covalently bonding with silica/silane surfaces. Such polymers are particularly useful in manufacturing polymeric compositions that are loaded with silica fillers, such as tire tread compounds. In any case, such controlled polymerizations are conducted in the presence of the free radical control agents made by the synthesis process of this invention.

The controlled polymerization can be a batch, semi-batch, or continuous process which provides excellent control of the polymer composition and morphology. The controlled polymerization will normally be carried out as an emulsion polymerization process.

Controlled polymerization requires the presence of a free radical control agent to control the course of polymerization while minimizing undesirable side reactions, such as chain termination. The control agent has characteristics that depend greatly on the details of the polymerization, including the mechanism for polymerization, the types of monomers being used, the type of initiation, the solvent system and the reaction conditions. The control agent may be a control agent for polymerization by a free radical mechanism, such as reversible-addition fragmentation transfer (RAFT), nitroxide-mediated polymerization (NMP), atom transfer radical polymerization (ATRP) and degenerative transfer (DT). Control agents for related controlled free-radical polymerization processes, such as diphenylethylene (DPE)-mediated polymerization and xanthate-based RAFT (MADIX) or a related mechanism involving stable free radicals. The control agent may be introduced into the emulsion system by many different methods, and the preferred method depends greatly on the particular embodiment being practiced. In some embodiments, the active control agent may be added directly to the reaction vessel in the form of a pure compound or as a component of a solution or mixture. In other embodiments, the active control agent may be generated in situ from chemical reactions occurring prior to, during or after emulsification.

Regardless of the method used to introduce or generate a control agent, the control agents suitable for the present invention offer one or more of the benefits associated with "living" polymerization kinetics. These benefits may include: (1) a linear dependence of the degree of polymerization as a function of time; (2) a linear dependence of the number-average molecular weight (Mn) on the extent of polymerization; (3) a constant number of polymer molecules and active centers that is sensibly independent of conversion; (4) a narrow molecular weight distribution, with Mw/Mn generally less than 2, preferably between 1.1 and 1.8, and often below 1.4; and (5) essentially complete conversion of monomer to polymer with the ability to continue polymerization upon addition of more monomer.

All polymerization reactions must be initiated. For some monomers, such as styrene for example, thermal self-initiation can occur without the need for additional reagents. For many other monomers, initiation may be accomplished by adding an agent to trigger one or more chemical reactions that ultimately produces an intermediate capable of propagating polymerization. These agents often are referred to as "initiators."

The type of initiators suitable for the present invention depend greatly on the details of the polymerization, including the mechanism for polymerization, the types of monomers being used, the type of control agent, the solvent system and the reaction conditions. Many different types of initiators have been investigated.

The initiator may be an initiator for polymerization by a free radical mechanism, such as ATRP, NMP, DT, RAFT or a related mechanism involving stable free radicals. Typically, suitable initiators for free radical polymerization are reagents or combinations of reagents that are capable of producing free radicals. Other methods for producing free radicals, including exposure to ionizing radiation ($^{60}$Co γ-rays), photochemical reactions, or sonication, will be evident to those of skill in the art as suitable methods for initiating free radical polymerization.

Some representative examples of free radical initiators which are commonly used include the various peroxygen compounds such as potassium persulfate, ammonium persulfate, benzoyl peroxide, hydrogen peroxide, di-t-butyl peroxide, dicumyl peroxide, 2,4-dichlorobenzoyl peroxide, decanoyl peroxide, lauryl peroxide, cumene hydroperoxide, p-menthane hydroperoxide, t-butyl hydroperoxide, acetyl acetone peroxide, dicetyl peroxydicarbonate, t-butyl peroxyacetate, t-butyl peroxymaleic acid, t-butyl peroxybenzoate, acetyl cyclohexyl sulfonyl peroxide, and the like; the various azo compounds such as 2-t-butylazo-2-cyanopropane, dimethyl azodiisobutyrate, azodiisobutyronitrile, 2-t-butylazo-1-cyanocyclohexane, 1-t-amylazo-1-cyanocyclohexane, and the like; the various alkyl perketals, such as 2,2-bis-(t-butylperoxy)butane, ethyl 3,3-bis(t-butylperoxy) butyrate, 1,1-di-(t-butylperoxy)cyclohexane, and the like. Persulfate initiators, such as potassium persulfate and ammonium persulfate, are especially useful in such aqueous emulsion polymerizations.

Polymerization can also be initiated with free radicals that are generated utilizing redox initiators, such as combinations of chelated iron salts, sodium formaldehyde sulfoxylate, and organic hydroperoxides. Some representative examples of such organic hydroperoxides include cumene hydroperoxide, paramenthane hydroperoxide, and tertiary butyl hydroperoxide. Tertiary butyl hydroperoxide (t-BHP), tertiary butyl peracetate (t-BPA) and "azo" initiators, such as azobisiobutyronitrile (AIBN), are preferred for use in generating free radicals.

In batch operations, the polymerization time can be varied as desired; it may vary, for example, from a few minutes to several days. Polymerization in batch processes may be terminated when monomer is no longer absorbed, or earlier, if desired, e.g., if the reaction mixture becomes too viscous. In continuous operations, the polymerization mixture may be passed through a reactor system of any suitable design. The polymerization reactions in such cases are suitably adjusted by varying the residence time. Residence times vary with the type of reactor system and the size of the reactors, for example, from 10 to 15 minutes to 24 or more hours.

Surfactants are essential in the case of controlled emulsion polymerizations, and suitable surfactants include any compound or mixture of compounds capable of stabilizing colloidal aqueous emulsions. Generally, surfactants are amphiphilic molecules that reduce the surface tension of liquids, or reduce interfacial tension between two liquids or a liquid and a solid. Surfactants may be small molecules or polymers, micelle-forming or non-micelle-forming, and may be anionic, cationic, zwitterionic or nonionic. In some embodiments of the present invention, mixtures of surfactants are used. The amount of surfactant used typically ranges from about 0.01 to about 200% by weight relative to the monomer, with a more preferred range being from about 0.1 to about 8% by weight and a more specifically preferred range being from about 0.5 to about 3% by weight. Those skilled in the art typically consider a number of factors when selecting surfactants for a particular application, including economic factors (see Detergents Handbook, McCutcheon Division, Manufacturing Confectioner Publishing Co, Glen Rock, N.J., 1999). Suitable anionic surfactants include substituted or unsubstituted hydrocarbyl sulfates, sulfonates, carboxylates, phosphonates and phosphates having between 6 and 30 carbon atoms per anionic functional group. Suitable cationic surfactants include substituted or unsubstituted hydrocarbyl ammonium salts having between 6 and 30 carbon atoms per cationic functional group. Suitable nonionic surfactants include amphiphilic amides having between 6 and 30 carbon atoms for each hydrocarboyl group and between 2 and 30 carbon atoms for ea A broad range of suitable surfactants is described in McCutcheon's Emulsifiers & ch hydrocarbyl amine group. For each surfactant, one or more hydrogen or carbon atom from the hydrocarbyl groups may have replaced with another atom selected from the group consisting of N, S, O, Si, F, Cl, Br and I. The hydrocarbyl may also have one or more hydrogen or carbon atom replaced with a functionality such as a keto, ester, amide, ether, thioether, hydroxyl and the like, and the hydrocarbyl may be part of a ring structure.

In some embodiments, useful surfactants include, for example, alkali metal and ammonium salts of: (i) alkylsulfates (alkyl radical: $C_8$ to $C_{18}$); (ii) alkylarylsulfonic acids (alkyl radical: $C_9$ to $C_{18}$); (iii) alkanesulfonic acids (alkyl radical: $C_8$ to $C_{18}$); (iv) succinate half-amides of alkylamines (alkyl radical: $C_8$ to $C_{18}$); (v) succinate half-esters of alkanols (alkyl radical: $C_8$ to $C_{18}$); (vi) alkanoic acids (alkyl radical: $C_8$ to $C_{18}$); (vii) alkylphosphates (alkyl radical: C, to $C_{18}$); (viii) alkylphosphonates (alkyl radical: $C_1$ to $C_{18}$); (ix) acylated sarcosine and taurine (acyl radical $C_8$ to $C_{18}$); and (x) sulfosuccinic acid diesters and diamides (alkyl radical: $C_4$ to $C_{18}$). In other embodiments, useful surfactant include, for example: (i) alkanol amides (alkyl radical: $C_2$ to $C_{18}$); (ii) quaternized amines (alkyl radical: $C_7$ to $C_{18}$), including amine oxide derivatives; (iii) quaternized nitrogen-containing heterocycles with pendant alkyls (alkyl radical: $C_4$ to $C_{18}$); (iv) betaine derivatives (alkyl radical: $C_8$ to $C_{18}$); and (v) amphiphilic block copolymers.

An important aspect of the present invention is in-situ emulsification, which is achieved by reacting a "latent surfactant" with a "surfactant activator" to produce the surfactant for controlled emulsion polymerization. As used herein, the term "latent surfactant" refers to a compound or mixture of compounds that: (i) is soluble in a monomer-containing solution that is not miscible with water; and (ii) is not independently capable of producing a stabilized colloidal microemulsion at conventional surfactant levels from simple gentle mixing of the compound or mixture of compounds with monomer-containing solution and water.

The term "surfactant activator" is used herein to describe a compound or mixture of compounds that: (i) is soluble in water; and (ii) is not independently capable of producing a stabilized colloidal microemulsion at conventional surfactant levels from simple gentle mixing of the compound or mixture of compounds with monomer-containing solution and water. For the present invention, water can be a reactant for in-situ emulsification reactions, but water alone cannot be the surfactant activator. The use of an in-situ emulsification technique in a controlled polymerization process that can be used in accordance with this invention is described in U.S. patent application Ser. No. 10/721,718, filed on Nov. 25, 2003) now published as U.S. Patent Application Pub. No. 2004/0127634. The teachings of U.S. patent application Ser. No. 10/721,718 are incorporated herein by reference in their entirety.

The fundamental principles for in-situ microemulsification are described by Prokopov and Gritskova (*Russ. Chem. Rev* 2001, 70, 791), who review its use in conventional free-radical polymerization of styrene using alkali-metal soaps prepared in situ via neutralization of fatty acids. As explained by Prokopov and Gritskova, the preparation of a carboxylate soap at a styrene-water interface during emulsification can produce a fine microemulsion because interfacial tension is decreased significantly by an abundance of emulsifier produced at the interface. By varying the nature of the carboxylic acid and the metal counter-ion used in the surfactant synthesis at the interface, it was possible to control the degree of dispersion and stability of the emulsion, as well as the resulting polystyrene latex produced via conventional free radical polymerization. In the present invention, the principles of in-situ microemulsification are expanded broadly to produce emulsions suitable for controlled polymerization via a wide range of methods utilizing conventional soap levels without added hydrophobes or specialized emulsification equipment.

In some embodiments, the surfactant for controlled polymerization may be produced by an acid/base neutralization reaction at the monomer/water interface. For some types of anionic surfactants, this may be accomplished, for example, via reaction of a monomer-soluble acid with an aqueous base, where the monomer-soluble acid is the latent surfactant and the base is the surfactant activator for in-situ emulsification. Suitable monomer-soluble acids include, for example, palmitic acid, oleic acid, dodecylbenzene sulfonic acid, lauryl sulfate, hexadecylsulfonic acid, dihexadecylphosphonic acid, hexadecylsuccinate half ester, and the monohexadecylamide of succinic acid. Suitable bases include, for example, hydroxides, carbonates and bicarbonates of alkali metal ions and quaternary ammonium ions, substituted and unsubstituted amines, and basic nitrogen-containing heterocycles. It will be evident to those skilled in the art that any aqueous base with a $pK_b$ less than about the $pK_a$ of the monomer-soluble acid also may be suitable. It also will be evident that hydroxides generated in situ via hydrolysis of moisture-sensitive compounds, such as sodium methoxide, sodium amide, potassium hydride and the like, also may be suitable as surfactant activators.

For some types of cationic surfactants, in situ synthesis during emulsification may be accomplished, for example, via reaction of a monomer-soluble base with an aqueous acid, where the monomer-soluble base is the latent surfactant and the acid is the surfactant activator. Suitable monomer-soluble bases include, for example, hexadecyldimethylamine, hexadecyldimethylamine oxide, and amphiphilic nitrogen-containing heterocycles. Suitable acids include for example mineral acids, sulfonic acids and phosphonic acids. It will be evident to those skilled in the art that any aqueous acid with a $pK_a$ less than about the $pK_b$ of the monomer-soluble base also may be suitable. It also will be evident that acids generated in situ via: hydrolysis of moisture-sensitive compounds, such as Lewis acids, acyl halides, acyl anhydrides, mineral acid anhydrides, hydrolyzable transition-metal halides, main group halides and the like, also may be suitable as surfactant activators.

In some embodiments, surfactant may be produced in situ by chemical reactions that attach hydrophilic functionality to a functionalized hydrophobe. For these embodiments, the functionalized hydrophobe is the latent surfactant and the reagent or reagents necessary for attaching the hydrophilic functionality serve as surfactant activator. For some types of surfactants this may be accomplished, for example, via reaction of a monomer-soluble electrophile with an aqueous nucleophile. Suitable electrophiles include for example: (i) hydrocarboyl halides; (ii) hydrocarboyl esters; (iii) hydrocarboyl anhydrides; (iv) hydrocarbyl isocyanates; (v) hydrocarbyl halides; and (vi) hydrocarbyl esters of sulfonic acids. Suitable surfactant activators include for example: (i) amine-functionalized hydrocarbylsulfates, hydrocarbylcarboxylates, hydrocarbylphosphates, hydrocarbylammonium salts; (ii) diethanol amine; (iii) diethylenetriamine and other aminoamines; (iv) amino-polyethyleneglycols and polyethylenegycol ethers; (v) aminoglycosides; (vi) aminobetaines; (vii) hydroxides of alkali metal ions and quaternary ammonium ions; and (viii) hydrocarbylamines.

For some types of surfactants, in-situ synthesis and emulsification may be accomplished by reaction of a monomer-soluble nucleophile with an aqueous electrophile. Suitable nucleophiles include for example, hexadecylamine and hexadecyldimethylamine. Suitable electrophiles include for example succinic anhydride, dimethylsulfate and 1,3-propanesultone.

Many other reactions can be used to synthesize surfactants in situ, and the specific embodiments illustrated above are not intended to preclude any combination of latent surfactant/surfactant activator that produces a surfactant during emulsification. It will be evident to those skilled in the art that other latent surfactant/surfactant activator combinations may be suitable when the chemistries of surfactant synthesis and controlled polymerization are compatible.

The practice of this invention is further illustrated by the following examples which are intended to be representative rather than restrictive of the scope of the subject invention. Unless indicated otherwise, all parts and percentages are given by weight.

EXAMPLE 1

Phase Transfer Preparation of
S-(3-triethoxysilylpropyl)-S'-benzyl trithiocarbonate In this experiment a 250 ml, three-neck round bottom flask equipped with a pot thermometer, nitrogen inlet, and condenser was charged with 100 ml of saturated sodium chloride brine, 5 grams of solid sodium chloride, 23.8 grams (0.10 mole) of 3-mercaptopropyltriethoxysilane, 7.6 grams (0.10 mole) of carbon disulfide, and 0.2 grams of Aliquat® 336 quaternary ammonium salt (made by the methylation of mixed tri-octyl/decyl amine). Then, a magnetic stir bar was placed into the flask and the contents were stir vigorously at room temperature (about 22° C. (77° F.)). While the mixture was being stirred 4.42 grams (~0.11 moles) of solid sodium hydroxide pellets were added to the flask and the mixture turns yellow in color. After about 15 minutes the temperature had increased to about 40° C. (104° F.). At that point, 12.6 grams (0.10 moles) of benzyl chloride was added and the temperature increased to about 65° C. (149° F.) and that temperature was maintained for about 20 minutes. It was noted that the lower aqueous phase became colorless. The mixture was then rapidly cooled in a water bath and 50 ml of chloroform was added with stirring prior to filtration. A small amount of gelled material was filtered off (about 3.2 grams). The two phase filtrate was separated. The lower chloroform layer was then stripped on a rotovap to give 35.0 grams of yellow oil (the theoretical yield was 40.3 grams). Thus, the crude yield was estimated to be about 87%. $C_{13}$, Proton and Si-29 NMR analysis reveal that the crude material contained about 87% of the expected benyzlic structure with some hydrolysis of alkoxy groups.

EXAMPLE 2

Preparation of S-(3-triethoxysilylpropyl)-S'-(1-phenylethane) trithiocarbonate

In the procedure utilized in this experiment a 500 ml, three-neck round bottom flask equipped with a pot thermometer, nitrogen inlet, and condenser was charged with 130 ml of saturated sodium chloride brine, 6.5 grams of solid sodium chloride, 30.94 grams (0.13 mole) of 3-mercaptopropyltriethoxysilane, 9.88 grams (0.13 mole) of carbon disulfide, and 0.26 grams of Aliquat® 336 quaternary ammonium salt. Then, a magnetic stir bar was placed into the flask and the contents were stirred vigorously at room temperature (about 22° C. (77° F.)). While the mixture was being stirred 5.75 grams (about 0.143 moles) of solid sodium hydroxide pellets were added to the flask. After about 15 minutes, the temperature had increased to about 53° C. (127° F.). At that point, 25.0 grams (0.13 moles) of 1-bromoethylbenzene was added to the flask and the temperature increased to about 65° C. (149° F.). The temperature was maintained at about 65° C. (149° F.) for about one hour before it was cooled to a temperature of about 45° C. (113° F.). Then, 200 ml of chloroform was added to the flask and the mixture was filtered using an oversized filter. No polymer gel was observed in this experiment. The liquid filtrate separated into an upper phase and a lower phase. The lower phase was separated and the solvent was removed at reduced pressure to give 47.1 grams of a clear orange liquid (the theoretical yield was 54.2 grams). Thus, the crude yield was 87%. $C_{13}$, Proton, and Si-29 NMR analysis reveal that the crude material to contain about 87% of the expected benyzlic structure with some hydrolysis of alkoxy groups.

EXAMPLE 3

Bulk Thermal Polymerization of Styrene Using Crude RAFT Agent

In this experiment a 250 ml three neck round bottom flask was charged with 100 grams of styrene monomer and 4.83 grams of the crude RAFT agent synthesized as the reaction product in Example 1. A magnetic stir bar was added to the flask and a pot thermometer, condenser, and nitrogen inlet were attached. The system was flushed with a slow nitrogen purge while the mixture was stirred and heated to a temperature of about 120° C. (248° F.). The solution became a homogeneous orange color at that temperature. It was stirred overnight and was maintained at a temperature of about 120° C. (248° F.). After about 24 hours of reaction time, the molten product was poured into a pan that was coated with Teflon® polymer. Then, 101 grams of the polystyrene synthesized was isolated. The theoretical yield was 99.5 grams. SEC analysis of the polymer showed a number average molecular weight (Mn) of 12,400 with a polydispersity index (PDI) of 1.08.

EXAMPLE 4

Bulk Thermal Polymerization of Styrene Using Crude RAFT Agent

In this experiment a 250 ml three neck round bottom flask was charged with 100 grams of styrene monomer and 5.0 grams of the crude reaction product (RAFT agent) made in Example 2. A magnetic stir bar was added to the flask and a pot thermometer, condenser, and nitrogen inlet were attached. The system was flushed with a slow nitrogen purge while the mixture was stirred and heated to a temperature of about 120° C. (248° F.). The solution turned to a homogeneous orange color at that temperature. The solution was maintained at the temperature of about 120° C. (248° F.) and stirring was continued overnight. After about 24 hours of reaction time, the molten product was poured into a pan that was coated with Teflon® polymer. Then, 101 grams of the polystyrene synthesized was isolated. The theoretical yield was 105 grams so the conversion attained was about 96%. Analysis of the polymer by size exclusion chromatography (SEC) showed that it had a number average molecular weight (Mn) of 9500 and a polydispersity index (PDI) of 1.08.

Experimental Summary

From Example 1 and Example 2, it is clear from the NMR data that the aqueous phase transfer process can readily prepare silane derivatives that contain both alkoxysilyl and benzylic functionality. The decoloration of the aqueous phase during the reaction (from yellow to colorless) also indicates that the intermediate silyltrithiocarbonate monoanion (yellow) being alkylated by the benzyl halide. Example 3 and Example 4 provide direct evidence by size exclusion chromatography (SEC) that the crude control agents from Example 1 and Example 2 can be used to yield polystyrene of controlled molecular weight and very narrow polydispersity.

While certain representative embodiments and details have been shown for the purpose of illustrating the subject invention, it will be apparent to those skilled in this art that various changes and modifications can be made therein without departing from the scope of the subject invention.

What is claimed is:

1. A free radical control agent of the structural formula:

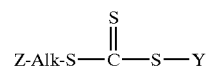

wherein Z is selected from the group consisting of

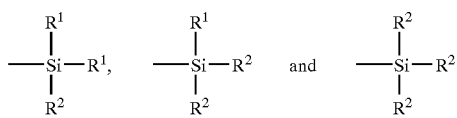

wherein R³ is an alkyl group of 1 to 4 carbon atoms, cyclohexyl or phenyl; wherein R² is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition.

2. A process for producing a polymer that is capable of covalently bonding to a silica/silicate surface which comprises polymerizing at least one monomer in the presence of the free radical control agent specified in claim 1.

3. The polymer made by the process specified in claim 2.

4. A rubbery polymer that is capable of covalently bonding to a hydroxyl group, said rubbery polymer being comprised of repeat units that are derived from a conjugated diolefin monomer and pendant functional groups of the structural formula:

$$Z\text{-Alk-S}-\underset{\underset{S}{\|}}{C}-S-$$

wherein Z is selected from the group consisting of

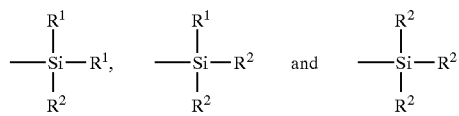

wherein R¹ is an alkyl group of 1 to 4 carbon atoms, cyclohexyl or phenyl; wherein R² is an alkoxy group of 1 to 8 carbon atoms or a cycloalkoxy group of 5 to 8 carbon; and wherein Alk is a divalent hydrocarbon of 1 to 18 carbon atoms.

5. A rubber composition which is comprised of the rubbery polymer specified in claim 4 and a filler having hydroxyl surface functionality.

6. A tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of a filler having hydroxyl surface functionality and the rubbery polymer specified in claim 4.

7. A process for producing a free radical control agent of the structural formula:

$$Z\text{-Alk-S}-\underset{\underset{S}{\|}}{C}-S-Y$$

wherein Z is selected from the group consisting of

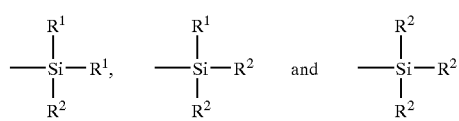

wherein R¹ is an alkyl group of 1 to 4 carbon atoms, cyclohexyl or phenyl; wherein R² is an alkoxy group of 1 to 8 carbon atoms or a cycloalkoxy group of 5 to 8 carbon atoms; wherein Alk is a divalent hydrocarbon of 1 to 18 carbon atoms; and wherein Y represents a functional group that is capable of activating a vinylic carbon toward free radical addition; said process comprising the steps of (1) reacting a mercaptosilane of the structural formula: Z-Alk-SH with carbon disulfide in the presence of (i) a phase transfer catalyst, (ii) an alkali metal hydroxide, and (iii) a saturated aqueous solution of a salt selected from the group consisting of LiF, LiCl, LiBr, Li₂SO₄, NaF, NaCl, NaBr, Na₂SO₄, KF, KCl, KBr, K₂SO₄, RbCl, RbBr, Rb₂SO₄, CsCl, CsBr, and Cs₂SO₄; to produce a trithiocarbonate salt; and (2) reacting the trithiocarbonate salt with a halogen containing compound of the structural formula X-Y to produce the free radical control agent.

8. A process as specified in claim 7 wherein the mercaptosilane of the structural formula: Z-Alk-SH is made by reacting a halogenated silane of the formula: Z-Alk-X with a compound of the formula MeSH in the presence of a phase transfer catalyst, wherein X represents a halogen atom, and wherein Me represents ammonium or an alkali metal.

9. A free radical control agent as specified in claim 1 wherein Y represents a functional group selected from the group consisting of —C(R')₂CN, —C(CH₃)₂Ar, —C(CH₃)₂COOR", —C(CH₃)₂CONHR", —C(CH₃)₂CH₂C(CH₃), —CH(CH₃)Ar, —CH₂Ar, —C(CH₃)₃, —CR'₂COOH, —C(R')(CN)—(CH₂)$_n$—COOH, and —C(R')(CN)—(CH₂)$_n$—OH; wherein R' represents a linear or branched hydrocarbon containing from 1 to 12 carbon atoms; wherein R" represents an alkyl group containing from 1 to about 8 carbon atoms: wherein Ar represents an unsubstituted or substituted phenyl, napthyl, anthracenyl, or pyrenyl group; and wherein n represents an integer from 1 to 8.

10. A process as specified in claim 7 wherein the mercaptosilane of the structural formula: Z-Alk-SH is reacted with the carbon disulfide in the presence of a saturated aqueous solution of sodium chloride.

11. A rubber composition as specified in claim 5 wherein the filler having hydroxyl surface functionality is a silicate clay.

12. A rubber composition as specified in claim 5 wherein the filler having hydroxyl surface functionality is silica.

13. A modified silica/silicate filler composition which is comprised of (1) a filler selected from the group consisting of silicate clays and silica; and (2) the free radical control agent specified in claim 1.

14. A rubbery polymer as specified in claim 4 wherein the conjugated diolefin monomer is 1,3-butadiene.

15. A rubbery polymer as specified in claim 4 wherein the conjugated diolefin monomer is isoprene.

16. A rubbery polymer as specified in claim 14 wherein the rubbery polymer is further comprised of repeat units that are derived from styrene.

17. A tire as specified in claim 6 wherein the filler having hydroxyl surface functionality is silica.

18. A tire as specified in claim 6 wherein the filler having hydroxyl surface functionality is a silicate clay.

* * * * *